US011673905B2

(12) United States Patent
Oger et al.

(10) Patent No.: US 11,673,905 B2
(45) Date of Patent: *Jun. 13, 2023

(54) TOPICAL COMPOSITION COMPRISING A SMALL RNA TIGER LILY EXTRACT AND METHOD OF COSMETIC CARE TO REDUCE SKIN SIGNS OF AGING

(71) Applicants: ELC Management LLC, Melville, NY (US); ISP Investments LLC, Wilmington, DE (US)

(72) Inventors: Elodie Oger, Vallauris (FR); Rachel Chabert, Grasse (FR); Isabelle Imbert, Cannes (FR); Jean-Marie Botto, Valbonee (FR); Nouha Domloge, Opio (FR); Joel Mantelin, Cannes (FR); Nadine Pernodet, Huntington Station, NY (US); Kelly Dong, Merrick, NY (US); Chia-Wen Chen, Eastchester, NY (US)

(73) Assignees: ISP INVESTMENTS LLC, Wilmington, DE (US); ELC MANAGEMENT LLC, Melville, NY (US)

( * ) Notice: Subject to any disclaimer, the term of this patent is extended or adjusted under 35 U.S.C. 154(b) by 1428 days.

This patent is subject to a terminal disclaimer.

(21) Appl. No.: 15/776,232

(22) PCT Filed: Nov. 10, 2016

(86) PCT No.: PCT/US2016/061302
§ 371 (c)(1),
(2) Date: May 15, 2018

(87) PCT Pub. No.: WO2017/087245
PCT Pub. Date: May 26, 2017

(65) Prior Publication Data
US 2020/0246252 A1   Aug. 6, 2020

(30) Foreign Application Priority Data

Nov. 17, 2015 (FR) ..................... 1502361

(51) Int. Cl.
| | |
|---|---|
| *A61K 8/44* | (2006.01) |
| *C07H 1/08* | (2006.01) |
| *A61K 8/60* | (2006.01) |
| *C07H 21/02* | (2006.01) |
| *A61Q 19/08* | (2006.01) |
| *A61K 8/9789* | (2017.01) |
| *C12N 15/10* | (2006.01) |
| *A61Q 19/00* | (2006.01) |
| *A61Q 17/04* | (2006.01) |
| *A61K 8/9794* | (2017.01) |

(52) U.S. Cl.
CPC ............... *C07H 1/08* (2013.01); *A61K 8/44* (2013.01); *A61K 8/606* (2013.01); *A61K 8/9789* (2017.08); *A61K 8/9794* (2017.08); *A61Q 17/04* (2013.01); *A61Q 19/00* (2013.01); *A61Q 19/007* (2013.01); *A61Q 19/08* (2013.01); *C07H 21/02* (2013.01); *C12N 15/1003* (2013.01); *C12N 15/1017* (2013.01); *A61K 2800/10* (2013.01); *A61K 2800/30* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 6,270,780 B1 | 8/2001 | Carson et al. | |
| 11,021,505 B2 * | 6/2021 | Oger | A61K 8/606 |
| 2003/0092168 A1 | 5/2003 | Lubrano et al. | |
| 2005/0222071 A1 | 10/2005 | Duranton et al. | |
| 2007/0003609 A1 | 1/2007 | Collin-Djangone et al. | |
| 2008/0161229 A1 | 7/2008 | Matsunaga et al. | |

FOREIGN PATENT DOCUMENTS

| | | |
|---|---|---|
| CN | 101601635 | 12/2009 |
| CN | 102776174 | 11/2012 |
| CN | 104138346 | 9/2016 |
| DE | 19820629 | 11/1999 |
| EP | 1723958 | 11/2006 |
| FR | 2831168 | 4/2003 |
| FR | 2912313 | 8/2008 |

(Continued)

OTHER PUBLICATIONS

DePaulo, et al.; Extraction of Double-Stranded RNA from Plant Tissues Without the Useof Organic Solvents; Plant Disease; The American Phytopathological Society; vol. 79; No. 3; pp. 246-248; Mar. 1995.

(Continued)

*Primary Examiner* — Susan Hoffman
(74) *Attorney, Agent, or Firm* — Yonggang Wu

(57) ABSTRACT

The invention relates to a topical composition comprising an extract of Tiger lily (*Lilium tigrinum*) enriched in low molecular weight RNA. The invention also relates to a method of cosmetic care including the topical application a composition comprising an extract of Tiger lily (*Lilium tigrinum*) in a physiologically acceptable medium, in order to reduce skin signs of aging and photo-aging. The invention is also directed to a cosmetic method of treatment to improve cell viability, to improve cell protection against particulate matter and against DNA damages, and to reduce cellular senescence.

8 Claims, 11 Drawing Sheets

(56) References Cited

FOREIGN PATENT DOCUMENTS

| FR | 2940112 | 6/2010 |
|---|---|---|
| JP | 2005-530812 | 10/2005 |
| JP | 2007-291062 | 11/2007 |
| JP | 2011-016760 | 1/2011 |
| JP | 5254535 | 8/2013 |
| WO | WO-84/03835 | 10/1984 |
| WO | WO-02/057289 | 7/2002 |
| WO | WO-03/101376 | 12/2003 |

OTHER PUBLICATIONS

Geusens, et al.; Cutaneous short-interfering RNA therapy; Expert Opinion on Drug Delivery; vol. 6; No. 12; pp. 1333-1349; Nov. 2009.

Zhang, et al.; Use of small RNA as antiaging cosmeceuticals; Journal of Cosmetic Science; vol. 64; pp. 455-468; Nov. 2013.

Jin, et al.; Phenolic Compounds and Antioxidant Activity of Bulb Extracts of Six Lilium Species Native to China; Molecules: A Journal of Synthetic Organic and Natural Product; vol. 17; No. 8; pp. 9361-9378; Aug. 2012.

PCT Int'l Search Report: Int'l Application No. PCT/US2016/061302; Completion Date: Jan. 17, 2017; dated Mar. 2, 2017. (16.73 (ORD)).

PCT Written Opin of the Int'l Searching Auth; Int'l Application No. PCT/US2016/061302; Completion Date: Jan. 17, 2017; dated Mar. 2, 2017. (16.73 (ORD)).

Zheng, et al.; Ethnobotanical study of medicinal plants around Mt. Yinggeling, Hainan Island, China; Journal of Ethnopharmacology; vol. 124; No. 2; pp. 197-210; Jul. 2009.

Li, et al.; Establishment of the total RNA extraction system for lily bulbs with abundant polysaccharides; African Journal of Biotechnology; vol. 10; No. 78; pp. 17908-17915; Dec. 2011.

Chinese Search Report from counterpart CN Application, Report dated Dec. 27, 2020.

FR Search Report from counterpart FR Application, Report dated Jun. 28, 2016.

Zumbo, P.; Phenol-chiorogorm Exraction; Weill Cornell Medical College: Laboratory of Christopher E. Mason, PH.D.; Dept. of Physicology & Biophysics; 2014.

\* cited by examiner

PBS

Full spectrum 0.5% Tiger Lili extract + Full spectrum

PBS

Full spectrum 0.2% Tiger Lili extract + Full spectrum 0.5% Tiger Lili extract + Full spectrum

TOPICAL COMPOSITION COMPRISING A SMALL RNA TIGER LILY EXTRACT AND METHOD OF COSMETIC CARE TO REDUCE SKIN SIGNS OF AGING

TECHNICAL FIELD

The present invention is in the field of cosmetics and more specifically in the field of topical compositions and methods for reducing skin signs of aging.

The invention relates to a topical composition comprising an extract of a Tiger lily (*Lilium tigrinum*) enriched in low molecular weight RNA.

The invention also relates to a method of cosmetic care including the topical application a composition comprising an extract of small RNA Tiger lily (*Lilium tigrinum*) in a physiologically acceptable medium, in order to reduce skin signs of aging and photo-aging.

BACKGROUND OF THE INVENTION

Small RNA and microRNA are cell components found in plants and in mammals that regulate physiological processes. In the skin, the main physiological processes are regulated by microRNA, acting as controllers of skin homeostasis: epidermal renewal, skin pigmentation regulation, dermal matrix expression, protection against oxidative stress.

The classic protocols for extracting ribonucleic acids (RNA, low molecular weight RNA) carried out in the laboratory involve the use of solvents such as phenol and chloroform, but these are toxic and are not considered to be suitable cosmetic solvents (Zumbo, P. 2014 "Phenol-chloroform Extraction", 2014; kit Sigma, mirPremier™ microRNA Isolation Kit). Document WO8403835 is known for example, and describes a method for obtaining an aqueous extract of plant embryos enriched with pure DNA, which method includes many processing steps, including processing with an anionic detergent and various solvents including chloroform and octanol, which may possibly leave toxic traces in the products obtained, and therefore cannot be used in cosmetics.

U.S. Patent application 2003/0092168 and FR2831168 are also known, and these describe a method for obtaining an extract rich in nucleic acids (DNA and/or RNA) from a plant material, particularly plant embryos or seeds rich in DNA or RNA. The method consists in extracting the plant material in the presence of cellulolytic enzymes in an aqueous medium at an initial pH of 9 to 13, wherein the pH tends towards neutrality, treating the extract with a protease and separating the insoluble matter to recover a purified aqueous extract. The lyophilized product obtained in this way may in particular contain from 0.1 to 1% by weight DNA, from 0.2 to 1.5% by weight RNA besides carbohydrates, proteins, minerals, vitamin B and lipids. According to the data provided in said document, the lyophilized product obtained thereby thus seems to contain in particular from 1 to 10 mg/L DNA and from 10 to 75 mg/L RNA.

In the context of the situation described above, on problem the invention is designed to solve is that of providing a new composition for topical application which includes solely RNA in the form of nucleic acids and which offers benefits for combatting aging of the skin by improving skin homeostasis and protection by supplying plant small RNA or microRNA.

The foregoing introduction is presented solely to provide a better understanding of the nature of the problems confronting the art and should not be construed in any way as an admission as to prior art nor should the citation of any reference herein be construed as an admission that such reference constitutes "prior art" to the instant application.

The inventors have indeed demonstrated that an extract of bulb of Tiger lily (*Lilium tigrinum*) enriched in low molecular weight RNA can reduce skin signs of aging and photoaging. More specifically they could show the extract can improve cell viability, cell protection against particulate matter and against DNA damages, improve skin extracellular matrix and reduce cellular senescence.

SUMMARY OF THE INVENTION

The main aspect of the present invention relates to a topical composition comprising an extract of Tiger lily (*Lilium tigrinum*) enriched in low molecular weight RNA (ribonucleic acid) with a maximum length of 150 nucleotides in a physiologically acceptable medium.

In another aspect, the invention relates to a method for treating skin to reduce skin signs of aging and photoaging comprising applying a topical composition comprising an effective amount of extract of Tiger lily (*Lilium tigrinum*) enriched in low molecular weight RNA, in a physiologically acceptable medium.

In yet another aspect, the invention also relates to a method to improve cell viability, to improve cell protection against particulate matter and against DNA damages, to improve skin extracellular matrix and to reduce cellular senescence, comprising applying a topical composition comprising an effective amount of extract of Tiger lily (*Lilium tigrinum*) enriched in low molecular weight RNA, in a physiologically acceptable medium.

DESCRIPTION OF THE DRAWINGS

Further embodiments of the present invention can be understood with the appended figures.

DETAILED DESCRIPTION

Figure 1:
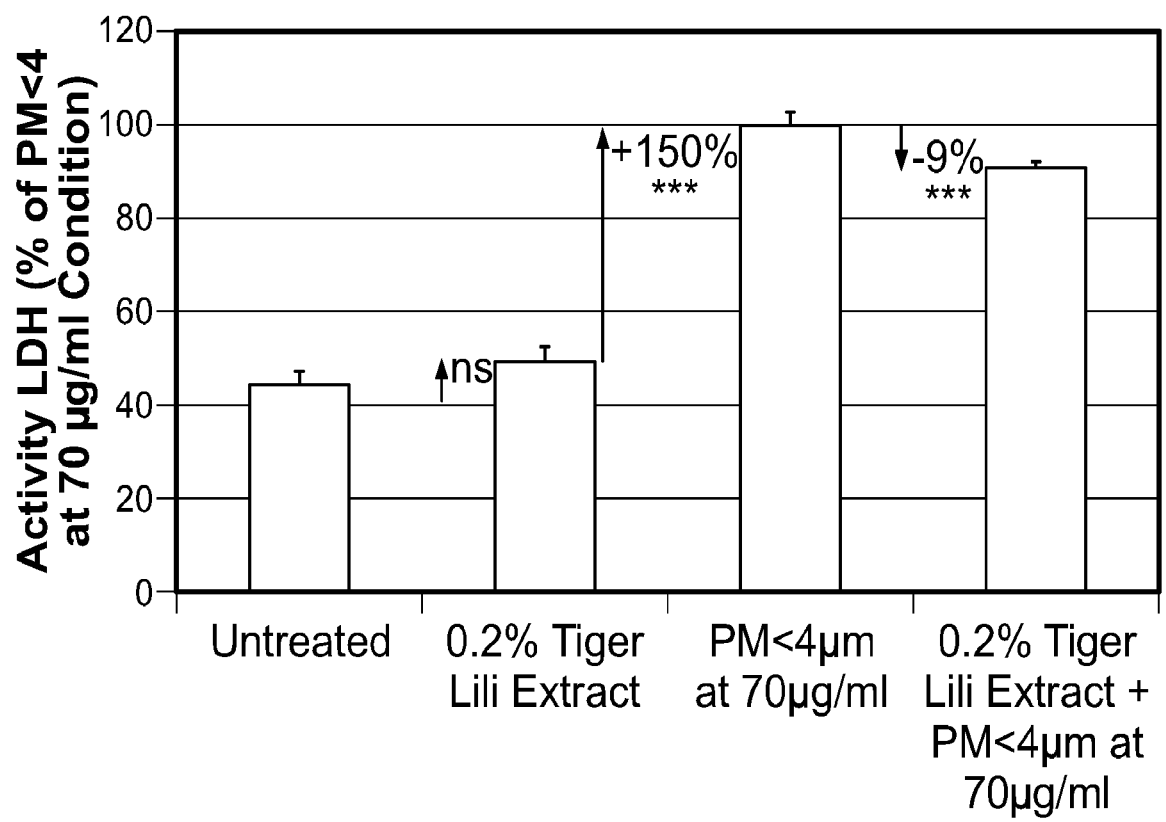
FIG. 1 illustrates evaluation of the Tiger lily (*Lilium tigrinum*) extract of the invention on the environmental stress resistance (Cellular viability measured by dosage of the Lactate DesHydrogenase (LDH) activity).

Detailed embodiments of the present invention are disclosed herein; however, it is to be understood that the disclosed embodiments are merely illustrative of the invention that may be embodied in various forms. Therefore, specific structural and functional details disclosed herein are not to be interpreted as limiting, but merely as a representative basis for teaching one skilled in the art to variously employ the present invention.

All terms used herein are intended to have their ordinary meaning unless otherwise provided. For the purposes of describing and claiming the present invention, the following terms are defined:

"Skin signs of aging and photo-aging" refers to all changes in the external appearance of the skin due to aging, such as, for example, thinning of the skin, sagging, loss of hydration and atonia, deep wrinkles and fine lines, loss of firmness and tone, dermal atrophy, loss of skin tone homogenization, or any other internal degradation of the skin resulting from exposure to ultraviolet radiation, liver spots and age spots. Liver spots also known as "Solar lentigo", "Lentigo senilis", "Old age spot", "Senile freckle", are blemishes on the skin associated with aging and photo-aging due to exposure to ultraviolet radiation from the sun. They range in color from light brown to red or black and are located in areas most often exposed to the sun, particularly the hands, face, shoulders, arms and forehead, and the scalp if bald.

"Anti-Aging Benefit" Anti-aging benefits include, but are not limited to, one or more of: (a) treatment, reduction, and/or prevention of fine lines or wrinkles, (b) reduction of skin pore size, (c) improvement in skin thickness, plumpness, and/or tautness; (d) improvement in skin suppleness and/or softness; (e) improvement in skin tone, radiance, and/or clarity; (f) improvement in procollagen and/or collagen production; (g) improvement in skin texture and/or promotion of retexturization; (h) improvement in skin barrier repair and/or function; (i) treatment and/or prevention of skin sagging or atrophy; (j) improvement in appearance of skin contours; (k) restoration of skin luster and/or brightness; (l) replenishment of essential nutrients and/or constituents in the skin; (m) improvement of skin appearance decreased by menopause; (n) improvement in skin moisturization and/or hydration; and (o) improvement of skin elasticity and/or resiliency and/or firmness.

"Physiologically acceptable" means that the active agent according to the invention, or a composition containing said agent, is suitable for coming into contact with the skin or a mucus membrane without provoking a toxicity or intolerance reaction.

"Physiologically acceptable medium" means a more or less fluid that may include, but are not limited to any additive or co-solvent commonly used in the cosmetic field as well as the adjuvant necessary for their formulation, humectants, surfactants, emulsifiers, etc. suitable for coming into contact with the skin or a mucus membrane without provoking a toxicity or intolerance reaction.

"Topical" or "topically" refers to applying the composition comprising the extract of Tiger lily of the present invention to the surface of a healthy area of the skin.

"Topical application" refers to the application or spreading of the peptide of the present invention, or a composition containing it, on the surface of the skin or a mucus membrane.

«small RNA», refers to low molecular weight non-coding RNA (ribonucleic acid), with a maximum length of 150 nucleotides, including any types of non-messenger small RNA, simple or double strand, such as micro RNA, interfering RNA, intronic RNA, nuclear or nucleolar small RNA or any fragment of RNA.

Whenever a term is identified by reference to a range, the range will be understood to explicitly disclose every element thereof. As a non-limiting example, a range of 1-10% will be understood to include 1%, 2%, 3%, 4%, 5%, 6%, 7%, 8%, 9%, and 10%, and all values between 1 and 10%.

Where two or more substituents are referred to as being "selected from" a group of enumerated alternatives, it is meant that each substituent can be any element of that group, independent of the identity of the other substituents.

"%" refers to % by weight, that is the weight percent of a component in relation to the total weight of the composition (i.e., including any carriers, vehicles, solvents, fillers, or other components added before application to the skin) unless otherwise provided.

What is described herein is a process for obtaining an extract of Tiger lily (*Lilium tigrinum*) enriched in low molecular weight RNA (ribonucleic acid) with a maximum length of 150 nucleotides, in a physiologically acceptable medium.

Small RNA comprise regulatory molecules that affect all aspects of cellular biology. Small RNA and in particular microRNA are cell components found in plants and in mammals that regulate physiological processes. In the skin, the main physiological processes are regulated by microRNA, acting as controllers of skin homeostasis: epidermal renewal, skin pigmentation regulation, dermal matrix expression, protection against oxidative stress. A Tiger lily extract containing specifically vegetal small RNA and vegetal microRNA is novel in the field of cosmetic. The expected benefits of the extract of bulb of Tiger lily (*Lilium tigrinum*) enriched in low molecular weight RNA is to improve skin homeostasis and protection by supplying plant small RNA/microRNA, and thereby providing skin anti-aging benefits.

The invention is directed to a topical composition comprising an extract of Tiger lily (*Lilium tigrinum*) enriched in low molecular weight RNA (ribonucleic acid) with a maximum length of 150 nucleotides, in a physiologically acceptable medium.

The process of preparation of such plant extracts is described in the patent application filed in France under number 1502361.

Preparation of an Extract of Bulb of Tiger lily (*Lilium tigrinum*) Enriched in Low Molecular Weight RNA An aqueous extract enriched in small RNA of low molecular weight (maximum length of 150 nucleotides) is obtained starting from tiger lily bulb (*Lilium tigrinum*) of the lily family (Liliaceae).

In a first step, after defrosting and washing, 10% (w/w) of lily bulbs are mixed with distilled water, for example 100 g of bulbs are put in 1 kg of distilled water, then bulbs are grinded for 10 minutes with 10 mM final concentration of tetrasodic EDTA corresponding to 3.8 g for 1 Kg of final volume. At this step pH is adjusted between 10.5 and 11, corresponding to the optimal pH to enriched the extract in RNA of low molecular weight.

The solution is then put under agitation for 1 hour at 80° C. At this stage, temperature can vary between 50° C. and 80° C. and the time of agitation can also be of 30 minutes until 1 h, for this species 80° C. temperature for 1 hour is the optimal temperature to obtain the best results in term of RNA of low molecular weight content in the final extract. At the end of this step, sequential filtrations are done with decreasing filter porosity, from 20-50 μm to 7-20 μm, to remove solid raw material, then clarify the aqueous extract.

At this step, pH is measured, and if needed, adjusted between 6 and 6.5 to preserve small RNA of low molecular weight in the extract. Too acid pH could make small RNA precipitated.

Then filtrations are pursued until sterilizing filtration of 0.2-0.3 μm filter porosity. The final extract can be preserved by adding 30% of glycerin and 1.5% of phenoxyethanol.

The obtained aqueous extract is yellow in colour and contains from 10 to 25 g/kg of dry matter, 0.5 to 5 g/kg protein fragments, 5 to 20 g/kg of sugars, 100 to 500 mg/kg of phenolic compounds and 10 to 100 mg/kg of RNA of low molecular weight with maximum nucleotides length of 150.

Nevertheless, for lilies of the same species (*Lilium tigrinum*), the obtained extracts can present an important variability in term of composition, according to external factors such as the place of harvest, the crop year, the season, climatic conditions, etc.

In this example, we obtained more particularly, an aqueous extract containing 17.9 g/Kg dry weight, 2.1 g/Kg of protein fragments, 11.4 g/Kg of sugars, 200 mg/Kg of phenolic compounds and 54 mg/Kg RNA of low molecular weight with a maximum length of 150 nucleotides. The extract is then diluted and preserved by adding 30% of glycerin and 1.5% of phenoxyethanol to obtain a final dry weight extract from 10 to 12 g/kg, a sugar concentration from 4 to 8 g/Kg, a protein fragments concentration from 0.5 to 1.5 g/kg, a phenolic compounds concentration from 50 to 200 mg/kg, a content in small RNA of low molecular weight with a maximum length of 150 nucleotides from 15 to 45 mg/kg.

Physico-chemical analysis done on the final extract showed that in this example, Tiger lily extract has a dry weight of 10 g/kg, contains 1 g/kg of protein fragments, 5.8 g/kg of sugars, 100 mg/kg of phenolic compounds, and 30 mg/kg of RNA of low molecular weight with a maximum length of 150 nucleotides. The gel electrophoresis performed to analyze the nucleic acid content of the extract showed that the RNA is of molecular weight equal or less than 150 nucleotides length and that the extract is totally free of DNA (deoxyribonucleic acid).

The main object of the invention is a cosmetic composition for topical application comprising a small RNA extract of bulb of Tiger lily (*Lilium tigrinum*), in a physiologically acceptable medium, wherein the said extract of Tiger lily comprises, in 30% glycerin and 1.5% of Phenoxyethanol, a dry weight from 10 to 12 g/kg, a sugar concentration from 4 to 8 g/Kg, a protein fragments concentration from 0.5 to 1.5 g/kg, a phenolic compounds concentration from 50 to 200 mg/kg and a content in RNA with a maximum length of 150 nucleotides from 15 to 45 mg/kg.

In a preferred embodiment the small RNA Tiger lily extract according to the invention has a dry weight of 10 g/kg, contains 1 g/kg of protein fragments, 5.8 g/kg of sugars, 100 mg/kg of phenolic compounds, and 30 mg/kg of RNA of low molecular weight with a maximum length of 150 nucleotides.

In another embodiment, the extract of Tiger lily (*Lilium tigrinum*) enriched in low molecular weight RNA of the present invention is present in the composition of the invention in a concentration between 0.1 to 5%, preferably 0.2 to 2.5%, based on the total weight of the composition.

The topical composition of the present invention may in particular be in the form of an aqueous, hydro-alcoholic or oily solution; an oil-in-water or a water-in-oil emulsion or multiple emulsions; aqueous or anhydrous gel; colloid. These compositions can also be in the form of creams, suspensions, or powders, suitable for application on the skin, mucous membranes, lips and/or skin appendages. These compositions may be more or less fluid and have the appearance of a cream, a lotion, a milk, a serum, a pomade, a cream, a paste or a foam. They may also be in solid form, such as a stick, or be applied to the skin in aerosol form. In one embodiment, the composition of the present invention is a cosmetic care composition.

The topical composition of the present invention include any additive commonly used in the cosmetic field as well as the adjuvant necessary for their formulation, such as co-solvents (ethanol, glycerol, benzyl alcohol, humectant, etc.), thickening agents, diluents, emulsifiers, antioxidants, coloring agents, sunscreens, pigments, fillers, preservatives, perfumes, odor absorbents, essential oils, trace elements, essential fatty acids, surfactants, film-forming polymers, chemical or mineral filters, hydrating agents or thermal water, and so on. It is possible, for example, to cite water-soluble polymers of a natural type, such as polysaccharides, or polypeptides, cellulosic derivatives of the methylcellulose or hydroxypropyl cellulose type, or synthetic polymers, poloxamers, carbomers, siloxanes, PVA or PVP, and in particular polymers sold by the ISP company.

In any case, a person skilled in the art will make sure that these adjuvants as well as their proportions are chosen so as not to counteract the advantageous properties sought in the composition according to the invention. These adjuvants may, for example, be present in concentrations ranging from 0.01 to 20% of the total weight of the composition. When the composition of the invention is an emulsion, the fatty phase may represent 5 to 80% by weight and preferably 5 to 50% by weight with respect to the total weight of the composition. The emulsifiers and co-emulsifiers used in the composition will be chosen from those conventionally used in the field considered. For example, they can be used in a proportion ranging from 0.3 to 30% by weight, with respect to the total weight of the composition.

Of course, the small RNA extract of Tiger lily of the present invention can be used alone or in association with other active ingredients. For example, the cosmetic care composition of the present invention contains, in addition, at least one other active ingredient intended to improve physiological functions of the skin, such as regenerating, anti-aging, anti-wrinkle, thickening, anti-free radical, anti-glycation, hydrating, antibacterial, antifungal, keratolytic, muscle relaxing, exfoliating, and toning ingredients, ingredients stimulating the synthesis of dermal macromolecules or energy metabolism, ingredients modulating cutaneous differentiation, pigmentation or depigmentation, ingredients stimulating microcirculation, sunscreens or metalloproteinase inhibiting ingredients.

In one embodiment, the composition of the present invention will comprise, in addition to the small RNA extract of Tiger lily of the present invention:

sunscreens, ultraviolet and Infrared screens
anti-free radical ingredients,
DHEA (dehydroepiandrosterone),
dehydroacetic acid (DHA),
natural or synthetic phytosterols,
alpha- and beta-hydroxyacids, silanols,
sugar amines, glucosamine, D-glucosamine, N-acetyl-glucosamine, N-acetyl-D-glucosamine, mannosamine, N-acetyl mannosamine, galactosamine, N-acetyl galactosamine,
polyphenols, isoflavones, flavonoids, such as grape extract, pine extract, olive extract,
lipids such as ceramides or phospholipids,
animal oils such as squalenes or squalanes,
vegetal oils, such as almond oil, coconut oil, castor oil, jojoba oil, olive oil, rapeseed oil, peanut oil, sunflower oil, wheat germ oil, corn germ oil, soybean oil, cotton oil, alfalfa oil, poppy oil, pumpkin seed oil, evening primrose oil, millet oil, barley oil, rye oil, safflower oil, passion oil, hazelnut oil, palm oil, apricot kernel oil, avocado oil, calendula oil, ethoxylated vegetable oils, or shea butter, The abovementioned compounds can be natural, such as peptide hydrolysates of plants, or also synthetic, such as peptide compounds.

The invention is also directed to a the cosmetic use of a topical composition comprising an effective amount of extract of Tiger lily (Lilium tigrinum) enriched in low molecular weight RNA, to reduce skin signs of aging and photo-aging.

The invention is also directed to a method for treating skin to reduce skin signs of aging and photoaging comprising applying a topical composition comprising an effective amount of extract of Tiger lily (Lilium tigrinum) enriched in low molecular weight RNA, in a physiologically acceptable medium.

The invention is also directed to a method to improve cell viability, to improve cell protection against particulate matter and against DNA damages, and to reduce cellular senescence, comprising applying a topical composition comprising an effective amount of extract of Tiger lily (Lilium tigrinum) enriched in low molecular weight RNA, in a physiologically acceptable medium.

In a particular embodiment the invention provides a method of cosmetic care to improve cell protection against pollution and cell protection against particulate matter.

In another embodiment the invention provides a method of cosmetic care to improve cell protection against UV induced DNA damages.

Other advantages and features of the invention will become clearer in view of the following examples provided for illustrative and non-limiting purposes.

EXAMPLE 1: EVALUATION OF THE SMALL RNA TIGER LILY (LILIUM TIGRINUM) EXTRACT ON THE ENVIRONMENTAL STRESS RESISTANCE (CELLULAR VIABILITY)

The purpose of this study is to show the effect of the Tiger lily (Lilium tigrinum) extract on the cellular viability, after an environmental stress. The environmental stress is induced by pollution particulate matter application (PM<4 µm; NIST2786). Cellular viability is measured by a dosage of the Lactate DesHydrogenase (LDH) activity. The LDH is an oxydoreductase enzyme which catalyzes the conversion of pyruvate in lactate. Its activity is linked to the presence of lesions and toxicity in tissues and cells.

Protocol: Normal human keratinocytes were treated twice a day for 48 hours with a solution of Tiger lily (Lilium tigrinum) extract, according to the invention, diluted at 1/500 eme in the culture medium, leading to a final concentration of 0.2% vol/vol. 24 hours before the end of treatments, the PM<4 µm were applied at 70 µg/ml.

After the treatments, a LDH activity assay was performed according to the supplier recommendation: «Lactate Dehydrogenase Activity Assay kit» (Sigma-Aldrich®; MAK066).

Results: As showed in FIG. 1, treatments with the Tiger lily (Lilium tigrinum) extract at 0.2% for 48 hours didn't show any impact on LDH activity and thus on cellular viability. PM<4 µm application at 70 µg/ml for 24 hours induced a highly significant (Student's t-test) increase of the LDH activity, underlying a strong decrease of cellular viability. Treatments with Tiger lily (Lilium tigrinum) extract at 0.2% for 48 hours in parallel to the PM<4 µm application significantly decrease LDH activity induced by the environmental stress.

Conclusion: Tiger lily (Lilium tigrinum) extract at 0.2% reduced the impact of the environmental stress on the keratinocyte viability.

EXAMPLE 2: EVALUATION OF THE SMALL RNA TIGER LILY (LILIUM TIGRINUM) EXTRACT ON DNA DAMAGE AFTER UV STRESS

The purpose of this study is to show the positive effect of the Tiger lily (Lilium tigrinum) extract on DNA damage after UV stress. DNA damage are quantified using a «Comet assay» also known as «Single Cell Gel Electrophoresis» (SCGE); a micro-electrophoretic technique that enables the detection of single and double strand DNA breaks in individual cells.

Protocol: Normal human fibroblasts were treated twice a day for 48 hours with a solution of Tiger lily (Lilium tigrinum) extract, according to the invention, diluted at 1/500 eme in the culture medium, leading to a final concentration of 0.2% vol/vol. 24 hours before the end of treatments, cells were irradiated with 100 mJ/cm$^2$ UVB.

After the treatments, cells were included in an agarose gel and lysed in a buffer containing detergents and salt. DNA is denatured and a short electrophoresis is carried out (25V, 300 mA, 30 minutes). After a propidium iodide staining, the unbreak DNA looks like a sphere of 25-35 µm of diameter. The DNA of an injured cell stretches toward the anode in proportion to the number of breaks. The detected lesions include strand breaks and alkali labile sites. Olive et al. (1990) defined the «Tail Moment» parameter which takes into account the comet length (µm) and the percentage of DNA in its distal part.

Figure 2:
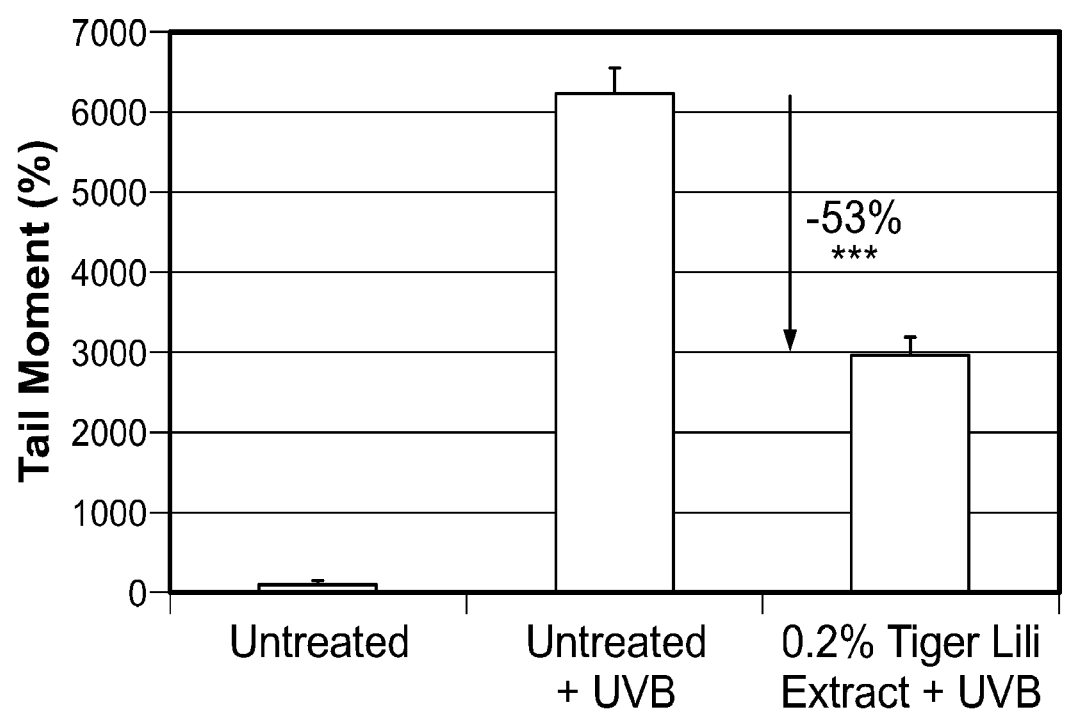
FIG. 2 illustrates evaluation of the Tiger lily (*Lilium tigrinum*) extract of the invention on DNA damage after UV stress (DNA damage are quantified using a «Comet assay».

Results: As shown in FIG. 2, UV stress induced a highly significant increase (Wilcoxon test) of DNA damage. Treatments with the Tiger lily (Lilium tigrinum) extract at 0.2% for 48 hours in parallel to the UV irradiation significantly decrease DNA damage induced by UV.

Conclusion: The Tiger lily (Lilium tigrinum) extract applied at 0.2% protected cells against DNA damage induced by UVB.

EXAMPLE 3: EVALUATION OF THE SMALL RNA TIGER LILY (LILIUM TIGRINUM) EXTRACT ON AGING, BY EXTRACELLULAR MATRIX EVALUATION, AND ON THE SENESCENCE

The purposes of this study are first to show the effect of the Tiger lily (Lilium tigrinum) extract on aging by the extracellular matrix (ECM) evaluation, regarding tropoelastin expression, and on the senescence, using beta-galactosidase activity senescent marker.

Protocol:

Evaluation of the Tropoelastin:

Normal human fibroblasts were aged by replicative senescence until P15.

Cells at P6 and P15 were treated twice a day for 48 hours with a solution of Tiger lily (*Lilium tigrinum*) extract, according to the invention, diluted at 1/500 eme in the culture medium, leading to a final concentration of 0.2% vol/vol.

For immunolabelling by anti-tropoelastin antibody, the cells were washed and fixed with cold methanol. The cells were then incubated in the presence of a specific anti-tropoelastin antibody (Abcam, ref. ab21605, rabbit polyclonal), and then a secondary suitable antibody, coupled with a fluorescent dye. After mounting in a particular medium, the slides were observed by epifluorescence microscope (Zeiss Axiovert 200M microscope). Fluorescence intensity was quantified by analyzing the image using Volocity® 6.3. software (PerkinElmer, Inc.).

Evaluation the Senescence:

Normal human fibroblasts were aged by replicative senescence until P15.

Cells at P15 were treated twice a day for 48 hours with a solution of Tiger lily (*Lilium tigrinum*) extract, according to the invention, diluted at 1/500 eme in the culture medium, leading to a final concentration of 0.2% vol/vol. A young control untreated P8 was added.

For SA beta-gal activity staining, the cells were first washed and fixed. They were then incubated overnight with beta-galactosidase stain solution. After mounting in a particular medium, the slides were observed by light microscopy (Nikon Eclipse E600 microscope). Blue intensity was quantified by analyzing the image using Volocity® 6.3. software. A normalization by the number of cells was performed.

Figure 3:
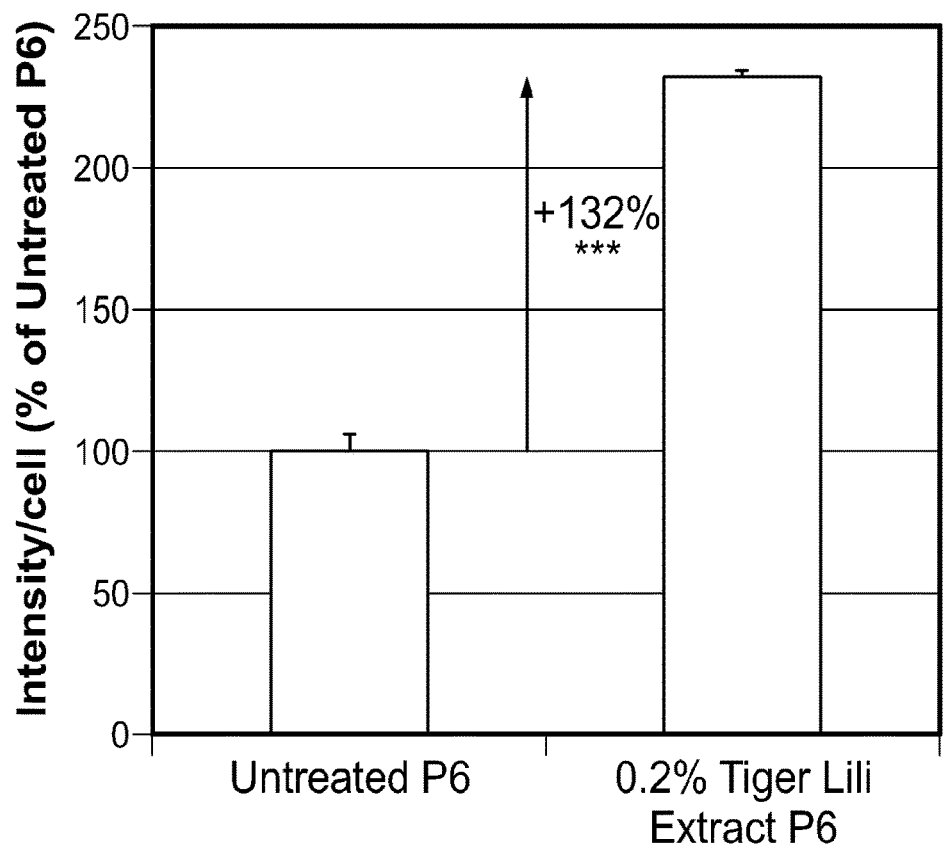
FIG. 3 illustrates evaluation of the Tiger lily (*Lilium tigrinum*) extract of the invention on aging, by extracellular matrix evaluation (tropoelastin expression).
Figure 3:
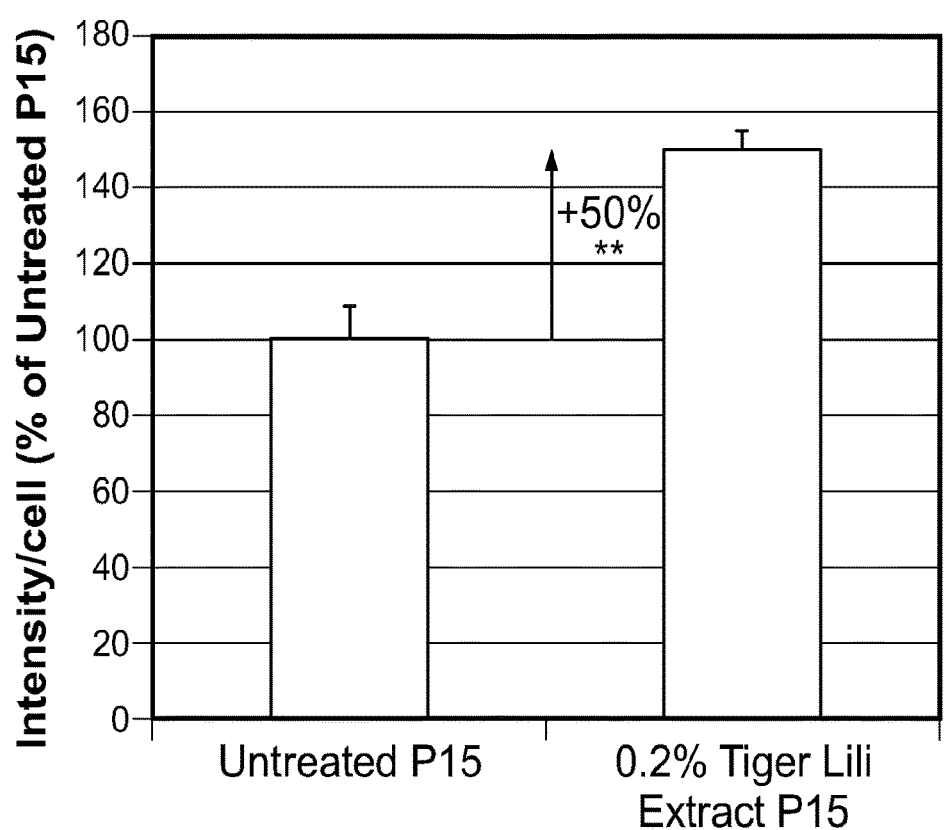

Results:

Evaluation of the Tropoelastin (FIG. 3):

The treatments with a solution of Tiger lily (*Lilium tigrinum*) at 0.2% for 48 hours showed a significantly highly increase (Student's t-test) in tropoelastin expression on fibroblasts, non-senescent (P6) and senescent (P15).

Figure 4:
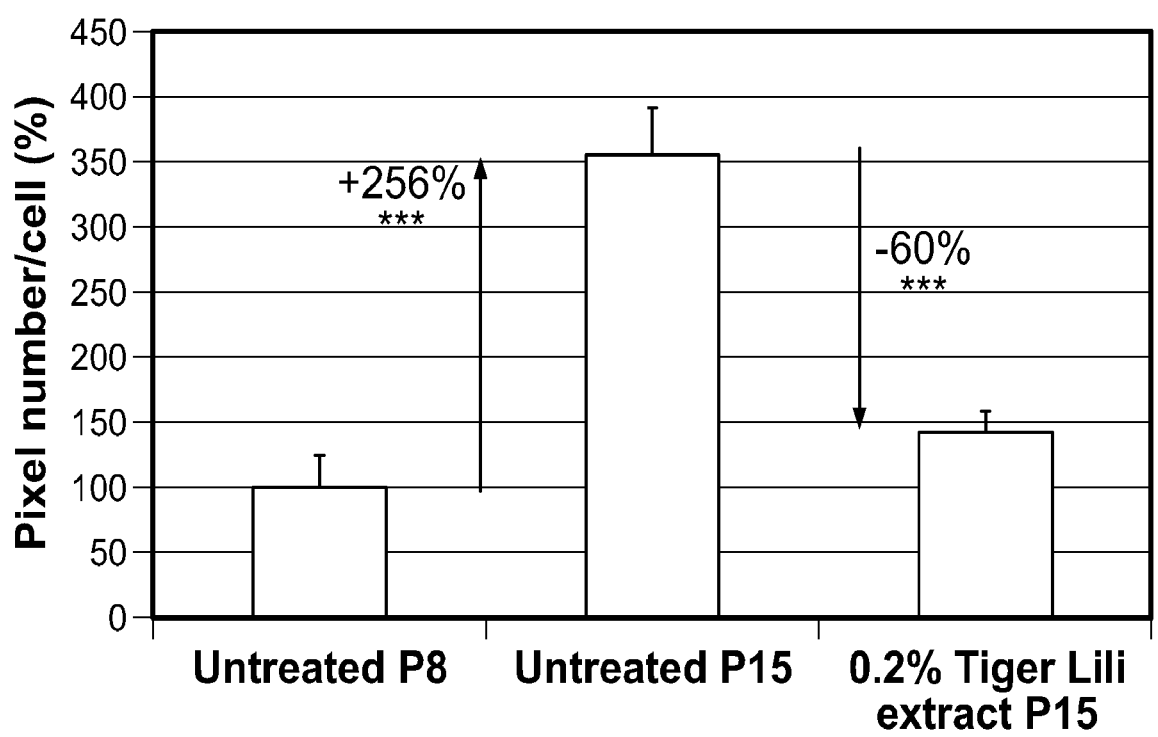
FIG. 4 illustrates evaluation of the Tiger lily (*Lilium tigrinum*) extract of the invention on aging, on the senescence (beta-galactosidase activity senescent marker).

Evaluation of the Senescence (FIG. 4):

As expected, beta galactosidase activity increased in replicative aged fibroblasts (P15) compared to young cells (P8). Treatments with a solution of Tiger lily (*Lilium tigrinum*) extract at 0.2% for 48 hours significantly reduced (Student's t-test) the induced senescence.

Conclusion: The Tiger lily (*Lilium tigrinum*) extract at 0.2%, preserved the ECM from aging by the stimulation of tropoelastin expression, in non-senescent and senescent cells, and reduced the replicative senescence.

EXAMPLE 4: EVALUATION OF THE SMALL RNA TIGER LILY (*LILIUM TIGRINUM*) EXTRACT ON SKIN PRESERVATION AGAINST PHOTO-AGING DAMAGE

The purpose of this study is to show the positive effect of the Tiger lily (*Lilium tigrinum*) extract on skin against photo-aging damage induced by UV stress. Fibrillin and tropoelastin, involved in the ECM structure, are evaluated.

Protocol: Normal human skin biopsies of 6 mm of diameter were maintained ex vivo in a specific culture medium (DMEM at 1 g/L, HAMF12, fetal calf serum et antibiotics). Biopsies were treated twice a day for 48 hours with a solution of Tiger lily (*Lilium tigrinum*) extract, according to the invention, diluted at 1/200 eme and 1/500 eme in PBS, leading to a final concentration of 0.5% and 0.2% vol/vol, respectively. The control condition is performed with PBS 1×. 24 hours before the end of the treatments, biopsies were irradiated using a UV full spectrum lamp at 100 mJ/cm2 (multiport 601 de solar light and co).

Evaluation of the Fibrillin:

For immunolabelling by anti-fibrillin antibody, tissues were frozen. Frozen skin biopsies were then cut and sections were fixed in cold acetone. A specific anti-fibrillin antibody (Abcam, ref. ab3090, mouse monoclonal) was applied, following by a secondary suitable antibody, coupled with a fluorescent dye. After mounting in a particular medium, the slides were observed by epifluorescence microscope (Zeiss Axiovert 200M microscope).

Evaluation of the Tropoelastin:

For immunolabelling by anti-tropoelastin antibody, tissues were fixed and embedded in paraffin. Embedded skin biopsies were then cut and sections were deparaffinized and rehydrated. Then, an unmasking protocol was performed before applying a specific anti-tropoelastin antibody (Abcam, ref. ab3090, rabbit polyclonal), and then a secondary suitable antibody, coupled with a fluorescent dye. After mounting in a particular medium, the slides were observed by epifluorescence microscope (Zeiss Axiovert 200M microscope).

Figure 5:
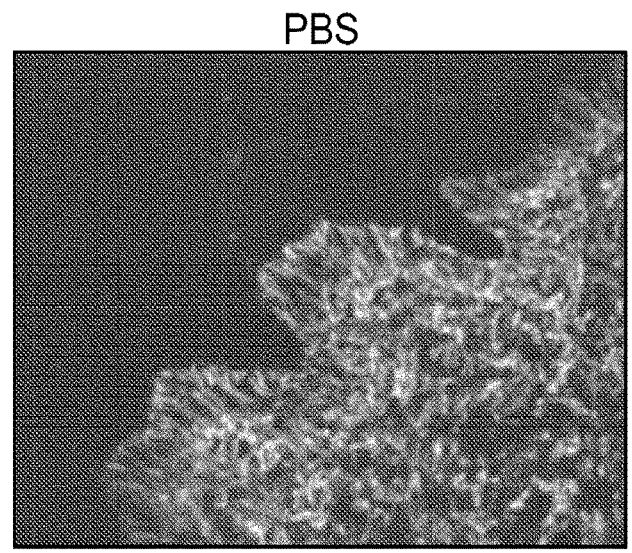
FIG. 5 illustrates evaluation of the Tiger lily (*Lilium tigrinum*) extract of the invention on skin preservation against photo-aging damage (evaluation of the Fibrillin involved in the ECM structure).
Figure 5:
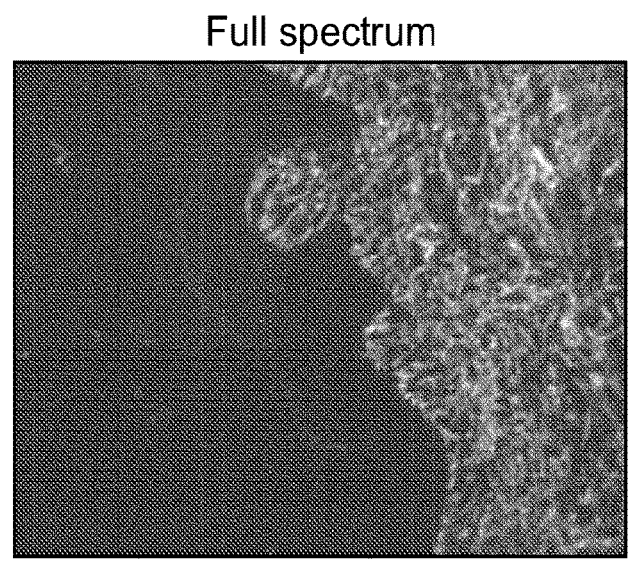
Figure 5:
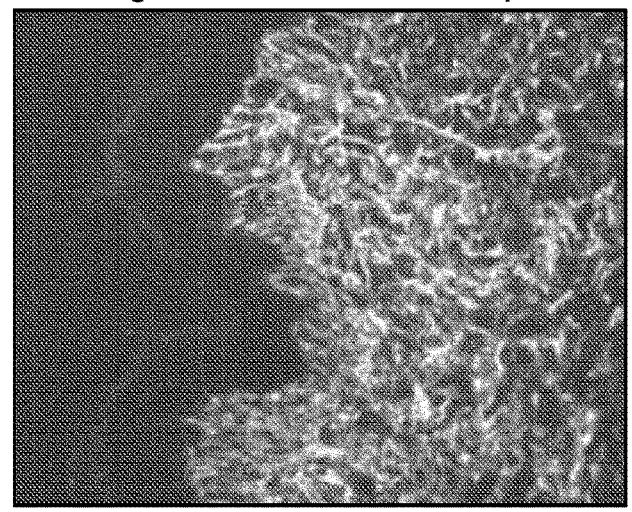

Results:

Evaluation of the Fibrillin (FIG. 5):

After UV stress, a dizorganization of fibrillin fibers was observed, as described in FIG. 5. Treatments with the solution of Tiger lily (*Lilium tigrinum*) extract at 0.5% in parallel to the stress visibly reduced UV impact on fiber organization.

Figure 6:
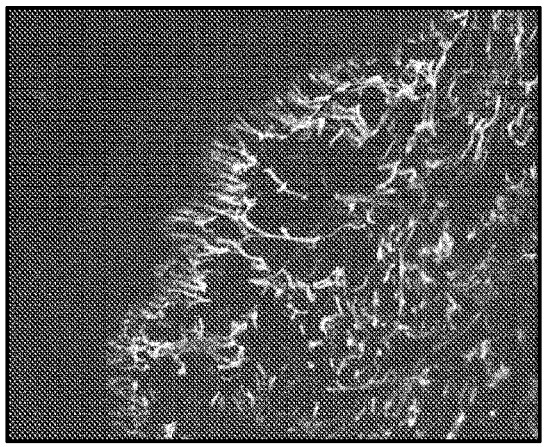
FIG. 6 illustrates evaluation of the Tiger lily (*Lilium tigrinum*) extract of the invention on skin preservation against photo-aging damage (evaluation of tropoelastin involved in the ECM structure).
Figure 6:
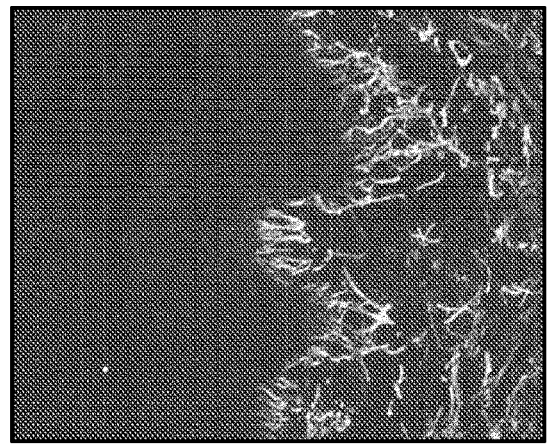
Figure 6:
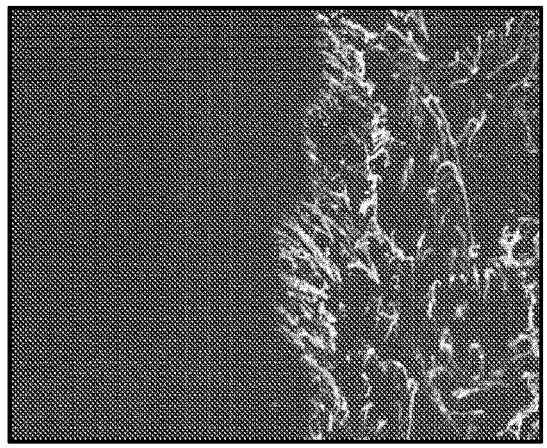
Figure 6:
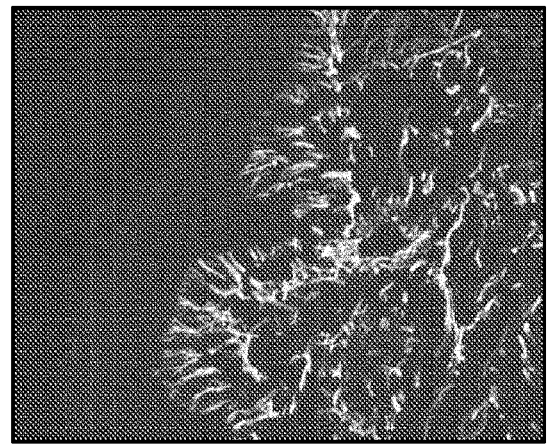

Evaluation of the Tropoelastin (FIG. 6):

After UV stress, a disorganization of tropoelastin fibers was observed, as described in FIG. 6. Treatments with the solution of Tiger lily (*Lilium tigrinum*) extract at 0.2% and 0.5% in parallel to the stress visibly reduced UVs impact on fiber organization.

Conclusion: After UV stress, a disorganization of tropoelastin and fibrillin fibers was observed. Treatments with Tiger lily (*Lilium tigrinum*) extract for 48 hours protected the ECM against UVs stress by reducing the fiber organization alteration, at 0.2% for fibrillin and at 0.2% and 0.5% for tropoelastin.

EXAMPLE 5: EVALUATION OF ELASTIN VOLUME IN FIBROBLAST TREATED WITH SMALL RNA *LILIUM TIGRINUM* EXTRACT

Figure 7:
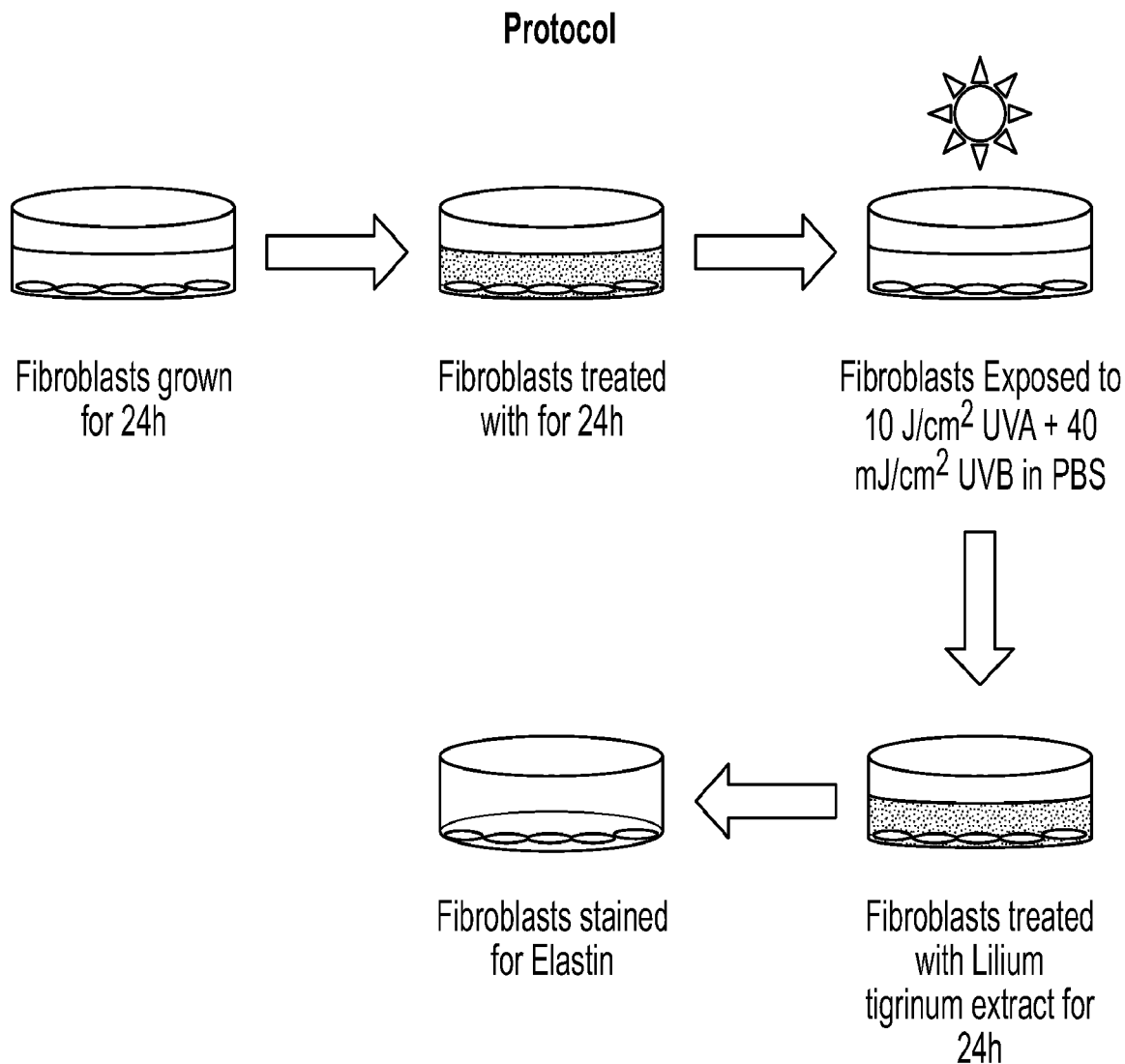
FIG. 7 illustrates the protocol for cell culture and treatment.

Protocol: Scheme of the protocol is shown in FIG. 7. Normal human dermal fibroblasts (NHDF) from a 19 y old donor at p10 and a 62 y old donor at p8 were plated in 35 mm glass bottom dishes at a concentration of 11,000 cells per dish and incubated for 24 h. A 20% stock solution of Tiger lily (*Lilium tigrinum*) was prepared by diluting 1.3 mL of Tiger lily (*Lilium tigrinum*) in 5.2 mL media (DMEM with 10% Bovine Calf Serum and 1% Penicillin/Streptomycin) and then filtering through a 0.2 μM PVDF filter. Tiger lily *Lilium tigrinum*) treatment solutions were prepared by diluting the stock solution in media to 0.2% and 2%. Cells were treated with Tiger lily (*Lilium tigrinum*) for 24 h. Cells were washed once with PBS and covered with a thin layer (1 mL) of PBS. Cells were irradiated with 10 J/cm² UVA+40 mJ/cm² UVB in a Dr. Gröbel irradiation chamber. Following irradiation cells were treated with Tiger lily (*Lilium tigrinum*) for 24 h.

At the conclusion of the treatment cells were rinsed with PBS, fixed in 4% Paraformaldehyde prepared in PBS for 15 min and perforated with 0.1% Triton prepared in PBS for 5 min Cells were blocked for 40 min in a block composed of 5% Goat Serum and 0.1% Triton prepared in PBS. Cells were stained for elastin by incubating cells in a 1:100 solution of rabbit antibody to Tropoelastin (Abcam, cat #ab21600) prepared in block overnight at 4° C. followed by a 1 h incubation in a 1:500 solution of AlexaFluor 594 goat anti-rabbit IgG (H+L) (Life Technologies, cat #A11012) prepared in block at room temperature. Cells were stained for actin and the nucleus by incubating cells in a solution of Phalloidin 488 (Life Technologies, cat #A12379) at 1:200 and DAPI (Life Technologies cat #D3571) at 1:36300, respectively, prepared in PBS for 20 min at room temperature. Stained cells were stored in PBS at 4° C. Images were captured with a Nikon A1 confocal microscope and a 60× oil immersion objective. Analysis was done with the Nikon Elements AR software by using the volume measurement tool.

Figure 8:
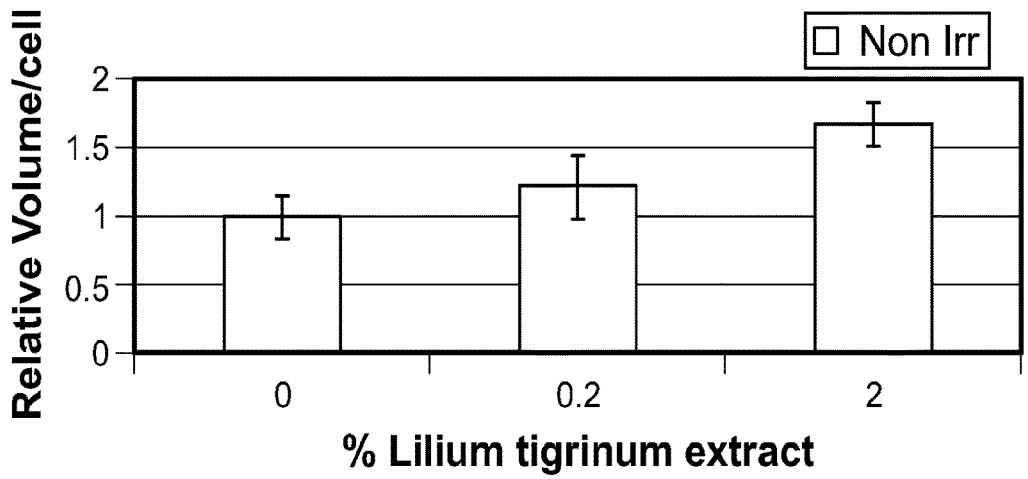
FIG. 8 illustrates the elastin volume in 19 year-old (19 y) fibroblasts treated with *Lilium tigrinum* extract of the invention.
Figure 8:
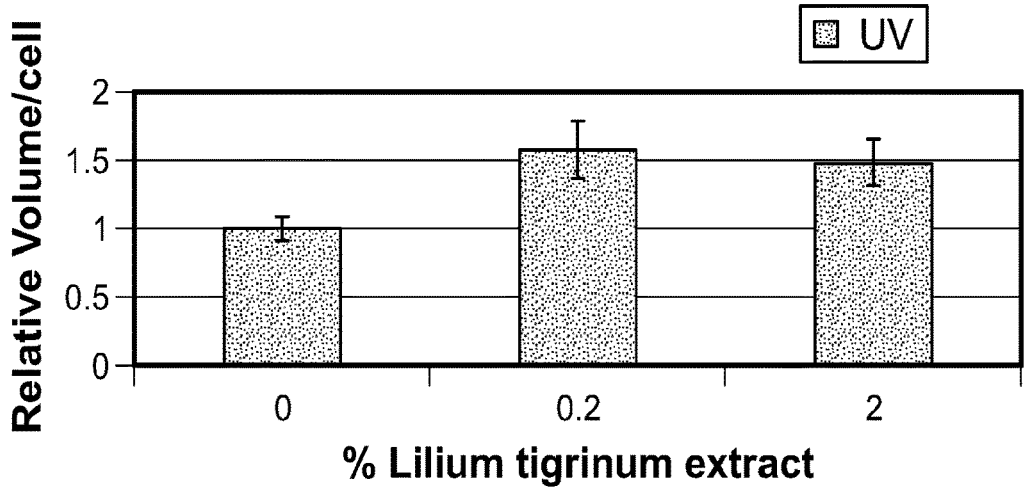
Figure 9:
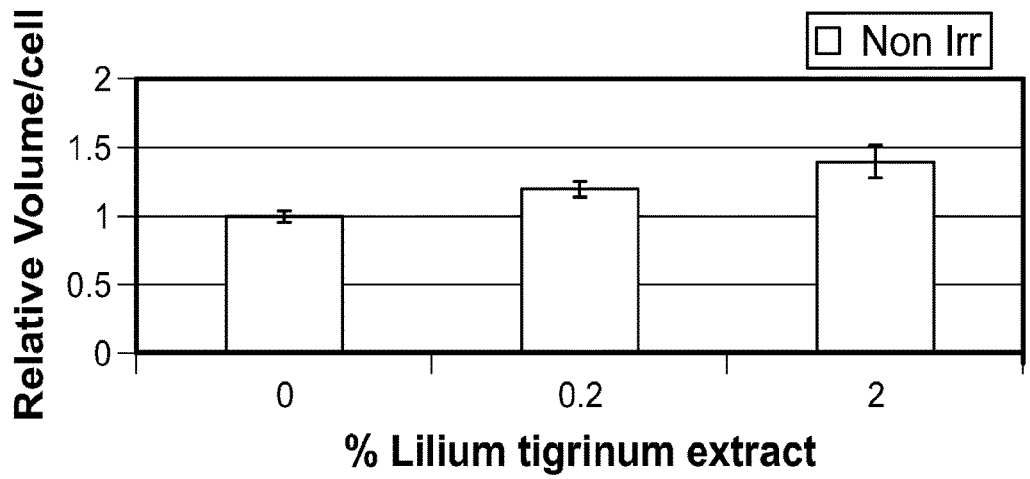
FIG. 9 illustrates the elastin volume in 62 year-old (62 y) fibroblasts treated with *Lilium tigrinum* extract of the invention.
Figure 9:
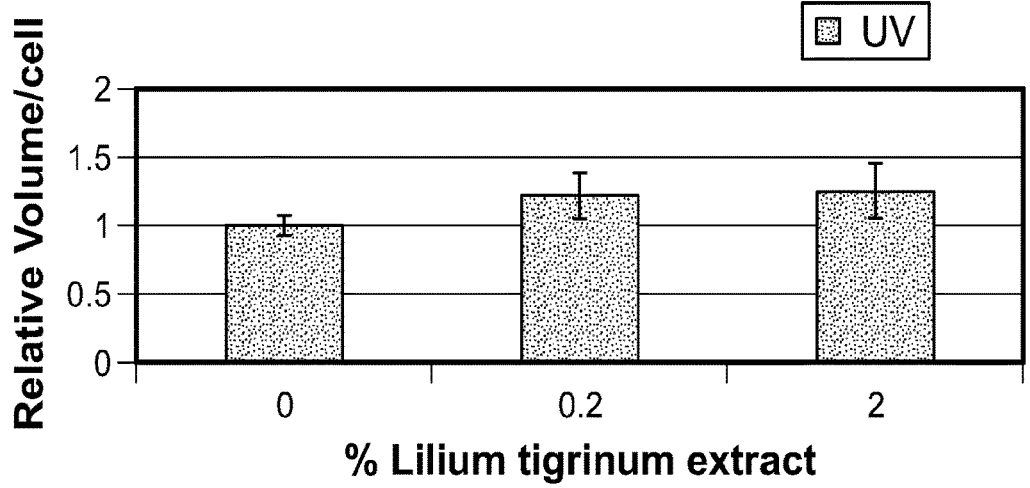

Results: Tiger lily (*Lilium tigrinum*) caused a dose dependent increase in elastin in the nonirradiated cells from the 19 y and 62 y old donors (FIGS. 8 & 9). The greatest increases achieved were 67% and 38% in the cells from the 19 y and 62 y old donors, respectively, when 2% Tiger lily (*Lilium tigrinum*) was used. Tiger lily (*Lilium tigrinum*) also increased elastin in irradiated cells from both aged donors, but the effect was not dose dependent. The largest increase was 79% in the cells from the 19 y old donor when 0.2% Tiger lily (*Lilium tigrinum*) was used and 46% in the cells from the 62 y old donor when 2% Tiger lily (*Lilium tigrinum*) was used.

Conclusion: Tiger lily (*Lilium tigrinum*) increased elastin in both irradiated and nonirradiated cells from both young and old donors.

EXAMPLE 6: EVALUATION OF DNA FRAGMENTATION IN FIBROBLASTS TREATED WITH SMALL RNA *LILIUM TIGRINUM* EXTRACT

Protocol: NHDF from a 19 y old donor at p10 and a 62 y old donor at p8 were plated in 60 mm dishes at a concentration of 80,000 cells per dish and incubated for 24 h. Cells were washed once with PBS and covered with a thin layer (2 mL) of PBS. Cells were irradiated with 10 J/cm² UVA+40 mJ/cm² UVB in a Dr. Gröbel irradiation chamber. Following irradiation cells were treated with 0.2% or 2% Tiger lily (*Lilium tigrinum*), prepared as described in example 5, for 6 h.

Cells were trypsinized, washed with PBS and suspended in PBS at 1×10⁵ cells/mL. Cells were then dispersed in melted agarose at 37° C. at a 1:10 ratio. 75 µl of the cell/agarose mixture was pipetted evenly on to each spot of the comet slide and then incubated at 4° C. for 10 minutes. Slides were immersed in cold lysis solution (Trevigen, cat #4250-050-01) overnight at 4° C. Slides were removed from the lysis solution and placed into an alkaline solution (300 mM NaOH, 1 mM EDTA, pH>13) at room temperature for 30 minutes. Then the slides were placed in an electrophoresis apparatus chilled in ice so that they were equidistant from the electrodes. Cold alkaline electrophoresis solution (300 mM NaOH, 1 mM EDTA, pH>13) was poured into the apparatus so that it just covered the slides. Electrophoresis ran for 30 minutes at 23V. After electrophoresis the slides were rinsed in H₂O and immersed in 70% EtOH for 5 min. Slides were removed from the EtOh solution and placed on a towel to air dry overnight. SYBR gold (Thermo, cat #11494) was diluted in TE buffer (10 mM Tris-HCl, 1 mM EDTA, pH 7.5) 1:30000. 100 µl of diluted SYBR gold was pipetted on to each spot. Slides were incubated at room temperature for 30 mM. Then slides were allowed to dry again after removing excess SYBR green from the slides and rinsing in H₂O. Images were captured with an EVOS microscope using the FITC filter with the 20× objective. The tail moments were determined with the Comet Score software from Tri Tek.

Figure 10:
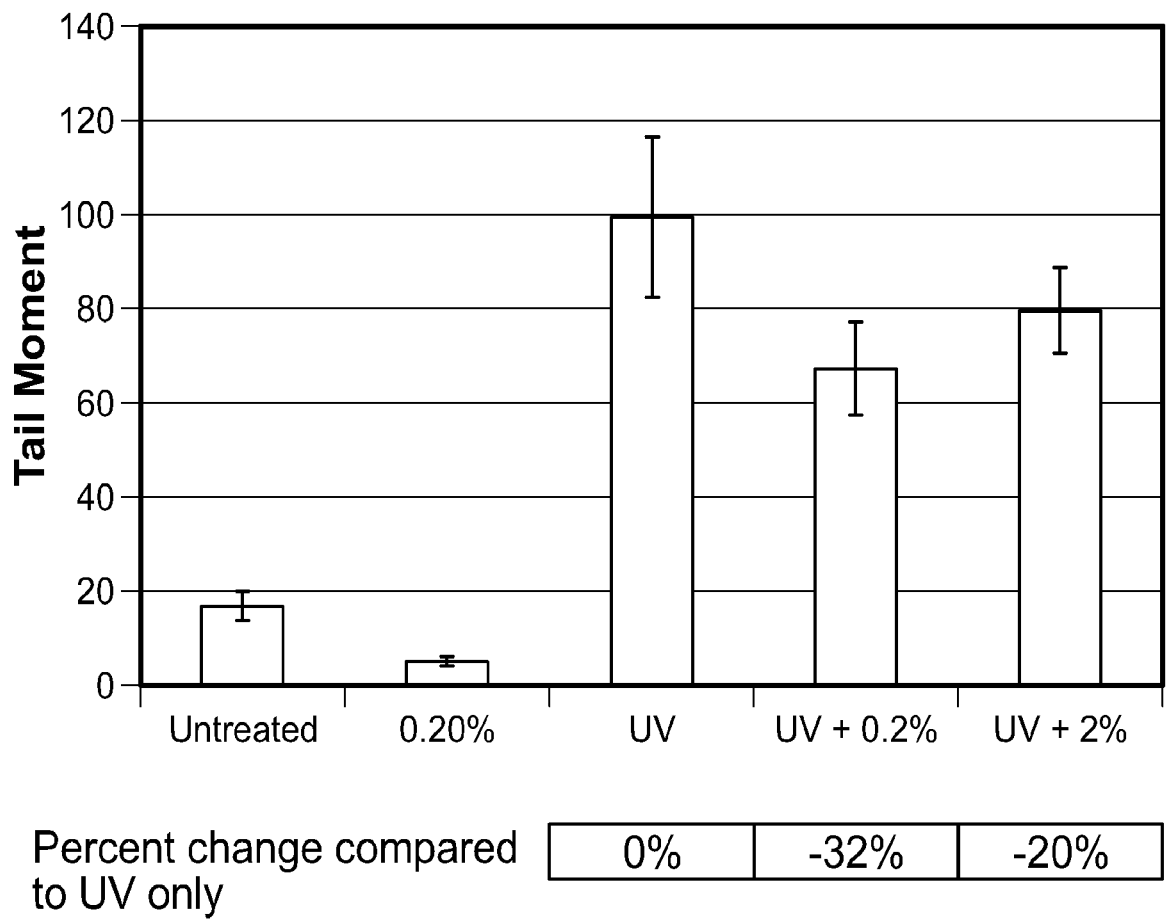
FIG. 10 illustrates the DNA fragmentation in fibroblasts from 19 year-old (19 y) donor treated with *Lilium tigrinum* extract of the invention.
Figure 11:
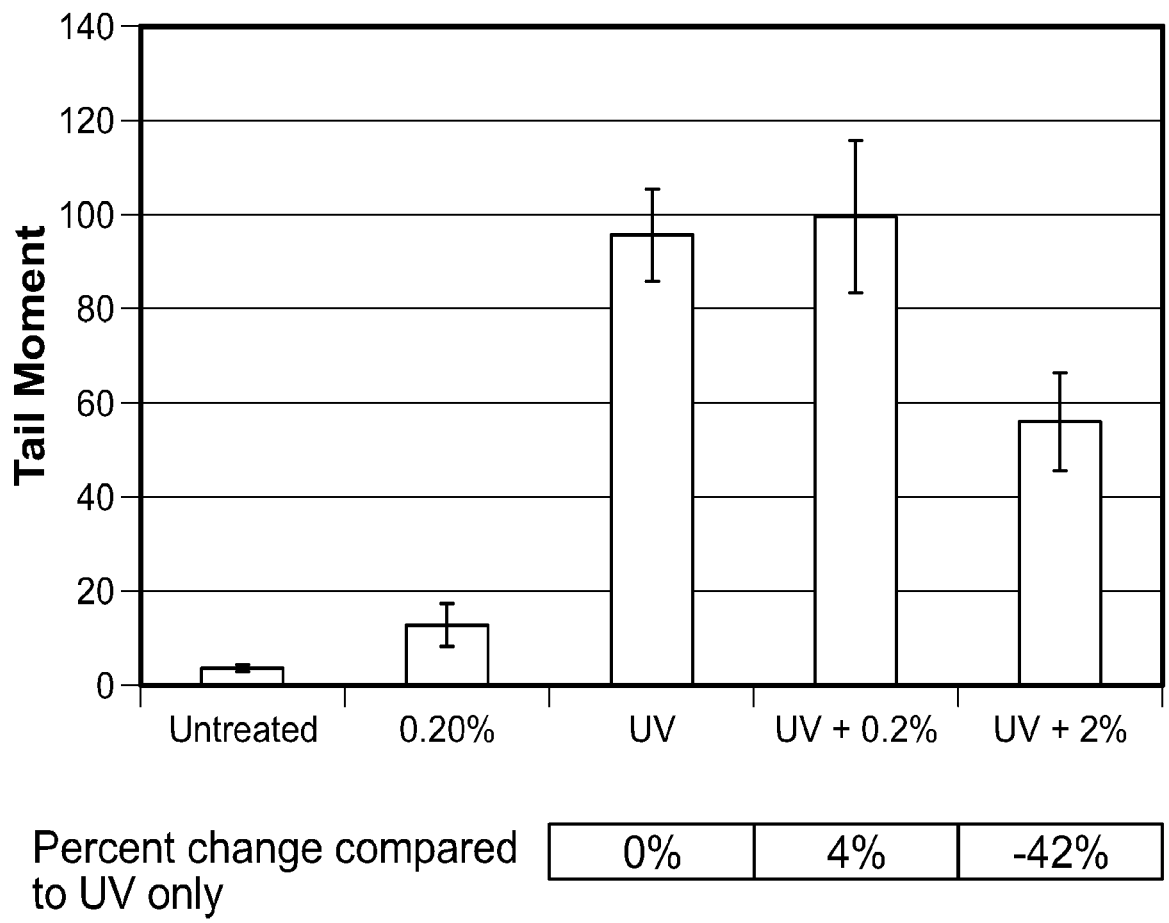
FIG. 11 illustrates the DNA fragmentation in fibroblasts from 62 year-old (62 y) donor treated with *Lilium tigrinum* extract of the invention.

Results: Treatment with either dose of Tiger lily (*Lilium tigrinum*) reduced UV induced DNA fragmentation in the cells from the 19 y old donor (FIG. 10). The largest decrease was 32% when 0.2% Tiger lily (*Lilium tigrinum*) was used. Only the 2% dose of Tiger lily (*Lilium tigrinum*) was able to reduce the UV induced DNA fragmentation in the cells from the 62 y old donor (FIG. 11). DNA fragmentation was reduced by 42%.

Conclusion: Tiger lily (*Lilium tigrinum*) was able to reduce UV induced DNA fragmentation in cells from both aged donors, but a higher dose of Tiger lily (*Lilium tigrinum*) was required for it to be effective in the cells from the older donor.

The invention claimed is:

1. A cosmetic composition for topical application comprising an extract of bulb of Tiger lily (*Lilium tigrinum*) and a physiologically acceptable medium, wherein the said extract of Tiger lily has a dry weight from 10 to 12 g/kg, a sugar concentration from 4 to 8 g/Kg, a protein fragments concentration from 0.5 to 1.5 g/kg, a phenolic compounds concentration from 50 to 200 mg/kg and a content in RNA with a maximum length of 150 nucleotides concentration from 15 to 45 mg/kg.

2. The cosmetic composition of claim 1, wherein the said extract of bulb of Tiger lily (*Lilium tigrinum*) is totally free of DNA.

3. The cosmetic composition of claim 1, wherein the said extract of bulb of Tiger lily (*Lilium tigrinum*) is present in the composition of the invention in a concentration between 0.1 to 5%, based on the total weight of the composition.

4. A method of cosmetic care comprising the topical application of a composition according to any of claims 1 to 3 to reduce skin signs of aging and photo-aging.

5. A method of cosmetic care comprising the topical application of a composition according to any of claims 1 to 3 to improve cell viability.

6. A method of cosmetic care comprising the topical application of a composition according to any of claims 1 to 3 to improve cell protection against pollution and cell protection against particulate matter.

7. A method of cosmetic care comprising the topical application of a composition according to any of claims 1 to 3 to improve cell protection against UV induced DNA damages.

8. A method of cosmetic care comprising the topical application of a composition according to any of claims 1 to 3 to reduce cellular senescence.

* * * * *